(12) United States Patent
Worch et al.

(10) Patent No.: US 6,524,718 B1
(45) Date of Patent: Feb. 25, 2003

(54) METALLIC OBJECT WITH A THIN POLYPHASE OXIDE COATING AND PROCESS FOR THE MANUFACTURE THEREOF

(75) Inventors: Hartmut Worch, Dresden (DE); Michael Thieme, Dresden (DE); Dieter Scharnweber, Dresden (DE); Sophie Rössler, Dresden (DE); Martina Stölzel, Kesselsdorf (DE)

(73) Assignee: Merck Patent GmbH (DE)

( * ) Notice: Subject to any disclaimer, the term of this patent is extended or adjusted under 35 U.S.C. 154(b) by 0 days.

(21) Appl. No.: 09/297,220

(22) PCT Filed: Oct. 23, 1997

(86) PCT No.: PCT/DE97/02465

§ 371 (c)(1),
(2), (4) Date: Jun. 21, 1999

(87) PCT Pub. No.: WO98/17844

PCT Pub. Date: Apr. 30, 1998

(30) Foreign Application Priority Data

Oct. 24, 1996 (DE) .......................... 196 43 555

(51) Int. Cl.$^7$ .......................... B32B 15/04; C25D 11/10
(52) U.S. Cl. .................. 428/472; 428/469; 428/624; 427/419.2; 427/419.5; 427/435; 205/322; 205/332; 205/324; 205/329
(58) Field of Search .................. 428/469, 472, 428/412, 293.4, 624, 639, 640, 470; 623/2.42, 3.29, 13.15, 13.18, 23.75, 901, 924, 925, 926; 427/419.5, 419.2, 435

(56) References Cited

U.S. PATENT DOCUMENTS

| | | | | |
|---|---|---|---|---|
| 3,609,867 A | * | 10/1971 | Hodosh | |
| 3,826,755 A | * | 7/1974 | Grimes et al. | |
| 4,097,935 A | * | 7/1978 | Jarcho | |
| 4,383,897 A | * | 5/1983 | Gillich et al. | |
| 4,399,021 A | * | 8/1983 | Gillich et al. | |
| 4,495,664 A | * | 1/1985 | Blanquaert | |
| 4,549,910 A | * | 10/1985 | Barba | |
| 4,581,336 A | * | 4/1986 | Malloy et al. | |
| 5,124,172 A | * | 6/1992 | Burrell et al. | |
| 5,603,818 A | * | 2/1997 | Brent et al. | |
| 5,840,387 A | * | 11/1998 | Berlowitz-Tarrant et al. | |

* cited by examiner

*Primary Examiner*—Deborah Jones
*Assistant Examiner*—Jennifer McNeil
(74) *Attorney, Agent, or Firm*—R W Becker & Associates; R. W. Becker

(57) ABSTRACT

A metallic object, having a metallic substrate of a valve metal or a valve metal alloy inclusive of intermetallic phases, and a thin polyphase oxide coating, is disclosed. The polyphase oxide coating has a metal oxide phase and at least one other organic and/or inorganic phase. The polyphase oxide coating is produced by bringing the metallic substrate into contact with an organic and/or inorganic component to be integrated into the polyphase oxide coating such that the inorganic and/or organic phases are present at or in the direct vicinity of the substrate surface and by simultaneously or subsequently anodically polarizing the substrate material in an electrolytic solution.

23 Claims, No Drawings

METALLIC OBJECT WITH A THIN POLYPHASE OXIDE COATING AND PROCESS FOR THE MANUFACTURE THEREOF

BACKGROUND OF THE INVENTION

The invention relates to a metallic object with a thin polyphase oxide coating and a process for the manufacture thereof. Objects with such an oxide coating exhibit, in addition to advantageous chemical and physical properties, high biocompatibility and can be used for a range of purposes due to their properties.

Known polyphase oxide coatings on metallic materials are produced by methods that utilize interdiffusion processes at high temperatures, or try to achieve a polyphase coating by deposition techniques with alternating coatings (flame spraying, PVD). Those coatings can also be produced by the sol-gel technology through a treatment at high temperatures. Common to all these methods is the fact that they are performed, at least partly, at process conditions that, particularly due to high temperatures, make the incorporation of organic phases impossible and, for inorganic phases, predominantly lead to the incorporation of waterfree high-temperature modifications.

A method for the production of modified, if necessary, oxide ceramic coatings on metals forming a barrier layer (valve metals; Ti, Al, Zr, etc.) is presented in EP 0545230. These oxide ceramic coatings are produced by plasma-chemical anodic oxidation in a chloride-free electrolyte bath having a pH-value of 2 to 8 by reaction at temperatures of −30° C. to +15° C. In this process no alloy is formed between the metal oxide phase and other inorganic phases. Due to the local plasma-chemical conditions at the place of oxide formation any organic substances are completely destroyed.

From DE-OS 36 27 249 a method is known by which conversion coatings on titanium surfaces are produced which consist of high-molecular organic compounds and tensides. These coatings are characterized by a very good adhesive strength, but are not realized through alloying of metal oxide with another phase. Furthermore, coating is executed at temperatures of 40–80° C. which excludes use of proteins.

From EP 0232791 and EP 0237053 methods are known in which a resorbable calcium phosphate ceramic, which is contained in oxides, is applied to titanium by anodic oxidation in aqueous electrolytes during spark discharge. The coatings thereby produced, however, do not consist of hydroxyapatite or fluoroapatite but of oxides and easily resorbable calcium phosphates. With the complete resorption of the calcium phosphate phases also the bioactive character of the implant is lost. Since also in this method the oxide coating formation occurs during spark discharge, any organic substances are completely distroyed.

In CA 2,073,781 A1 a method is presented in which an oxide coating is formed by anodic oxidation of the metals (titanium) or alloys (Ti- and Co-base alloys) used and, by subsequent cathodic polarization, calcium phosphate phases with different crystal modifications are deposited on the anodically formed oxide coating. The thereby produced coatings are to be treated with biologically active substances, such as collagens, BMP (bone morphogenetic proteins) or antibiotic substances. By using this method, the organic phases cannot be incorporated into the electrochemically formed surface coatings.

WO 92/13984 describes a method for deposition of bioactive coatings on conductive substrates. An electrolytic cell contains an inert anode and an electrolyte solution, which consists of an aqueous solution of ions of the ceramic and exhibits a pH-value of less than 8. The activated conductive substrate is immersed into the electrolyte solution and the potential between anode and conductive substrate set such that a ceramic coating is deposited on the conductive substrate by an increase of the pH-value at the interface between electrolyte solution and conductive substrate. It is a disadvantage of the solution that the coating is deposited only on the surface of the substrate so that, firstly, no load-resistant connection to it can be formed and, secondly, the coating is biologically completely resorbable.

It is an objective of the invention to create metallic objects with an improved surface coating by the production of thin polyphase oxide coatings under process conditions that allow the incorporation of organic and/or inorganic phases.

SUMMARY OF THE INVENTION

According to the invention the problem is solved by a metallic object with a thin polyphase oxide coating, whereby the oxide coating consists of a metallic oxide phase and at least one other organic and/or inorganic component. The metallic object consists of a valve metal, such as aluminum, titanium, tantalum, circonium, niobium, or its alloy, inclusive of intermetallic phases. Oxide coatings formed on these metals or alloys, respectively, show ionic conduction, at least when anodically polarized, and thereby, through anodic polarization, allow to vary the thickness of the oxide coatings within wide limits.

The distribution of the oxide coating growth to the phase boundaries metallic substrate material/oxide and oxide/environment can hereby be controlled through the selected electrochemical conditions. In this way two-layer oxide coatings can be produced, the outer layer of which may contain inorganic and/or organic phases, whereby the total thickness of the oxide coating as well as the distribution of the total thickness relative to the two coating componets can be controlled by selection of the electrochemical parameters potential, current and potential change rate. This makes it possible, depending on the particle size of the phases to be incorporated into the oxide coating, either to completely incorporate them or to adjust a defined degree of incorporation.

The organic component preferably consists of polymer materials, such as collagen, S-layer, polycarbonate and fullerenes, and/or biomolecules, and/or oligomers.

The inorganic component is preferably formed of inorganic fiber structures or calcium phosphate phases. It can be incorporated into the oxide phase of the metallic material, either alone or in connection with the organic component, or as a composite with the organic component.

The organic and/or inorganic component is inventively incorporated into the metallic oxide phase such that the polyphase oxide coating compares with an alloy. The organic component can extend beyond the polyphase oxide coating.

According to the invention, a thin polyphase oxide coating is produced on a metallic substrate material in such a way that first the metallic substrate material is brought into contact with the organic and/or inorganic phases to be integrated into the oxide coating such that these phases are present at, or in direct vicinity of the surface of the substrate.

The contact with the phases to be integrated into the oxide coating can be realized through adsorption, sedimentation, application, deposition or close mechanical contact, or by introduction into or application of suspensions of the phases to be integrated. Transportation of the phases to be integrated into the oxide coating to the substrate surface can be performed, or enhanced, by the application of electromagnetic fields.

Simultaneously or subsequently, in an electrochemical process step, the material forming the substrate surface is anodically polarized in an electrolyte solution.

On metallic materials that consist of valve metals or their alloys, this process step leads, through solution precipitation reactions, to an oxide growth at the phase boundary oxide coating/environment, followed by complete or partial integration of the phases at, or in the direct vicinity of, this phase boundary into the newly formed oxide coating.

The above process steps are, for the case of the integration of physiological organic components, carried out at or near room temperature so that both the structures and the functionality of these components is maintained.

The anodic polarization can be galvanostatically, potentiostatically or potentiodynamically performed until a predetermined formation potential has been reached. Criterion for the selection of the conditions of the anodic polarization is that the structure and functionality of the components to be integrated be optimally maintained in the process of the formation of the thin polyphase surface coatings.

The formation potential is selected to be in the range of 2 to 200 $V_{SCE}$.

The advantage of the coatings produced according to the invention is that due to the firm integration of the organic and/or inorganic component into the oxide coating of the metallic material, an improved force transmission and permanent enhancement of the biocompatibility are achieved.

DESCRIPTION OF PREFERRED EMBODIMENTS

With the aid of the following examples the invention will be explained in more detail.

EXAMPLE 1

A collagen solution is produced from acid-soluble, freeze-dried calf skin collagen. For this purpose, the type I collagen is dissolved in 0.01 M acetic acid and then adjusted to a concentration of 0.36 mg/ml at 4° C. and pH=3.5. The collagen molecules are reconstituted in two process steps: adjusting the pH-value to 7.4 in double-strength phosphate buffer, and raising the temperature to 34° C. After 3 hours the solution consists of native reconstituted collagen type-I fibrillae.

A cylindrical specimen of Ti6Al4V with a diameter of 9 mm and a thickness of 6 mm is ground (25–7 $\mu$m) and oxide-polished. Then the specimen is cleaned in alcohol and rinsed with deionized water. The thus prepared specimen is vertically inserted into the collagen solution so that the polished surface of the specimen is completely covered. Native collagen I is then adsorbed on the specimen's surface. Adsorption time is 20 minutes.

After adsorption, the metal specimen is taken out of the collagen solution, rinsed with distilled water, and placed as substrate electrode into a thermostat-controlled electrolysis cell of a three-electrode arrangement comprising a saturated calomel electrode as reference electrode and a platinum sheet as counter electrode. A weakly basic phosphate solution serves as electrolyte solution. The electrochemical reaction is performed in a double-jacket cell at 34° C. The substrate electrode is anodically polarized potentiodynamically in this arrangement at a potential change rate of 2 V/sec up to a formation potential of 100 V. The specimen is taken out of the electrolysis bath, rinsed with deionized water, and air-dried.

Electron-microscope analyses show native collagen I fibrillae, which are incorporated partly completely, partly partially into the oxide coating formed during the anodic polarization. A sectional preparation of the titanium oxide layer exhibits an oxide coating thickness of approx. 250 nm and shows the imprints of the incorporated fibrillae whose diameters correspond to those of the adsorbed fibrillae.

EXAMPLE 2

A collagen solution is produced from acid-soluble, freeze-dried calf skin collagen. For this purpose, the type I collagen is dissolved in 0.01 M acetic acid and then adjusted to a concentration of 1 mg/ml at 4° C. and pH=3.5. The collagen molecules are reconstituted in two process steps: adjusting the pH-value to 7.4 in double-strength phosphate buffer, and increasing the temperature to 34° C. After 3 hours the solution consists of native reconstituted collagen type-I fibrillae.

A cylindrical specimen of aluminum with a diameter of 9 mm and a thickness of 6 mm is ground (25–7 $\mu$m) and oxide-polished. Then the specimen is cleaned in alcohol and rinsed with deionized water. Collagen solution is dropped onto the thus prepared specimen so that the polished surface of the specimen is completely covered. Native collagen I is then adsorbed on the specimen's surface. Adsorption time is 40 minutes.

After the adsorption the collagen solution is rinsed off, and the aluminum specimen is rinsed with distilled water and placed as substrate electrode into a thermostat-controlled electrolysis of in a three-electrode arrangement comprising a saturated calomel electrode as reference electrode and a platinum sheet as counter electrode. A double-strength phosphate buffer pH=7.4 serves as electrolyte solution. The electrochemical reaction is performed in a double-jacket cell at 34° C. The substrate electrode is anodically polarized in this arrangement with a current density of 3 mA/cm$^2$ up to a formation potential of 40 V. Immediately afterward, this potential is fixed potentiostatically for 100 sec. After the polarization has been switched off, the specimen is taken out of the electrolysis bath, rinsed with deionized water, and air-dried.

Electron-microscope analyses show native collagen I fibrillae, which are partially incorporated into the oxide coating formed during the anodic polarization at those places where they were positioned on the air-formed oxide film of the aluminum.

EXAMPLE 3

A cylindrical specimen of Ti6Al4V with a diameter of 9 mm and a thickness of 6 mm is ground (25–7 $\mu$m) and oxide-polished. Then the specimen is cleaned in alcohol and rinsed with deionized water. In a vacuum apparatus the surface of the specimen is vapor-phase coated with $C_{60}$ molecules.

Then the specimen is placed as substrate electrode into a thermostat-controlled electrolysis cell of a three-electrode arrangement comprising a saturated calomel electrode as reference electrode and a platinum sheet as counter electrode. A double-strength phosphate buffer pH=7.4 serves as electrolyte solution. The electrochemical reaction is performed in a double-jacket cell at 34° C. The substrate electrode is anodically polarized in this arrangement with a current density of 0.5 mA/cm$^2$ for 500 sec. Formation potentials of up to approx. 8 V are measured. After the polarization has been switched off, the specimen is taken out of the electrolysis bath, rinsed with deionized water, and air-dried.

Electron-microscope analyses show a typical titanium oxide surface. FT-IR analyses in reflection mode verify the presence of $C_{60}$ molecules in this surface.

The specification incorporates by reference the entire disclosure of German priority documents 196 43 555.2 of Oct. 24, 1996, as well as of International Application PCT/DE97/02465 of Oct. 23, 1997.

The present invention is, of course, in no way restricted to the specific disclosure of the specification and drawings, but also encompasses any modifications within the scope of the appended claims.

What is claimed is:

1. Metallic object, having a metallic substrate consisting of a valve metal or a valve metal alloy inclusive of intermetallic phases, and a thin polyphase oxide coating, where said polyphase oxide coating is comprised of a first phase, wherein said first phase is a metal oxide phase, and a second phase, wherein said second phase is either an organic phase, an inorganic phase, or a combination of organic and inorganic phases, said polyphase oxide coating produced by bringing the metallic substrate into contact with either an organic component, an inorganic component, or a combination of organic and inorganic components to be integrated into said polyphase oxide coating such that said second phase is present at or adjacent to the substrate surface and by simultaneously or subsequently anodically polarizing said substrate material in an electrolytic solution, wherein said metallic substrate is selected from the group consisting of aluminum, titanium, tantalum, zirconium, niobium, or their alloys, inclusive of intermetallic phases.

2. Object according to claim 1, wherein said organic component is selected from the group consisting of polymer materials, biomolecules, oligomers, or a combination of polymer materials, biomolecules and oligomers.

3. Object according to claim 1, wherein said organic component is selected from the group consisting of collagen, S-layer, polycarbonate, or fullerenes.

4. Object according to claim 1, wherein said inorganic component consists of inorganic fiber structures or calcium phosphate phases.

5. Object according to claim 1, wherein only said inorganic component is incorporated into said polyphase oxide coating.

6. Object according to claim 1, wherein said inorganic component is incorporated into said polyphase oxide coating in combination with said organic component.

7. Object according to claim 1, wherein said inorganic component is incorporated into said polyphase oxide coating as a composite with said organic component.

8. Object according to claim 1, wherein said organic component, said inorganic component, or said combination of organic and inorganic components is completely incorporated into said polyphase oxide coating.

9. Object according to claim 1, wherein said organic component, said inorganic component, or said combination of organic and inorganic components is incorporated into said polyphase oxide coating and extends beyond it.

10. Process for manufacturing a thin polyphase oxide coating on a metallic substrate, said method comprising the steps of:

bringing a metallic substrate into contact with either an organic component, an inorganic component, or a combination of organic and inorganic components to be integrated into said polyphase oxide coating, such that either an organic phase, an inorganic phase, or a combination of inorganic and organic phases is present at or adjacent to the substrate surface, wherein said polyphase oxide coating is comprised of a first phase, wherein said first phase is a metal oxide phase, and a second phase, wherein said second phase is either an organic phase, an inorganic phase, or a combination of organic and inorganic phases, and wherein said metallic substrate is selected from the group consisting of aluminum, titanium, tantalum, zirconium, niobium, or their alloys, inclusive of intermetallic phases; and simultaneously or subsequently anodically polarizing said substrate material in an electrolytic solution.

11. Process according to claim 10, wherein said step of bringing into contact is realized by adsorption, sedimentation, application, deposition or close mechanical contact.

12. Process according to claim 10, wherein said step of bringing into contact is realized by introduction into or application of suspensions of said components to be integrated.

13. Process according to claim 10, wherein transportation of said components to be integrated into said polyphase oxide coating to the metallic substrate is performed, or enhanced, by applying electromagnetic fields.

14. Process according to claim 10, wherein the step of anodically polarizing is performed up to a formation potential of between 2 and 200 $V_{SCE}$.

15. Process according to claim 14, wherein the step of anodically polarizing is performed galvanostatically, potentiostatically or potentiodynamically.

16. Process according to claim 10, wherein said organic component is selected from the group consisting of polymer materials, biomolecules, oligomers, or a combination of polymer materials, biomolecules, and oligomers.

17. Process according to claim 10, wherein said organic component is selected from the group consisting of collagen, S-layer, polycarbonate, and fullerenes.

18. Process according to claim 10, wherein said inorganic component consists of inorganic fiber structures or calcium phosphate phases.

19. Process according to claim 10, wherein only said inorganic component is incorporated into said polyphase oxide coating.

20. Process according to claim 10, wherein said inorganic component is incorporated into said polyphase oxide coating in combination with said organic component.

21. Process according to claim 10, wherein said inorganic component is incorporated into said polyphase coating as a composite with said organic component.

22. Process according to claim 10, wherein said organic component, said inorganic component, or said combination of organic and inorganic components is completely incorporated into said polyphase oxide coating.

23. Process according to claim 10, wherein said organic component, said inorganic component, or said combination of organic and inorganic components is incorporated into said polyphase oxide coating and extends beyond it.

* * * * *